United States Patent [19]

Kadlec et al.

[11] Patent Number: 5,977,280
[45] Date of Patent: Nov. 2, 1999

[54] TERMINATING POST CURE WITH AMINO ACID ESTERS

[75] Inventors: Donald Anthony Kadlec; William James Schulz, Jr.; Shizhong Zhang, all of Midland, Mich.

[73] Assignee: Dow Corning Corporation, Midland, Mich.

[21] Appl. No.: 08/964,547

[22] Filed: Nov. 5, 1997

[51] Int. Cl.[6] .................................................. C08G 77/08
[52] U.S. Cl. ............................... 528/15; 528/31; 528/25; 524/731; 524/862; 424/401; 424/405; 424/70.12; 424/76.8; 424/76.1; 424/65; 424/63; 424/64; 523/122; 174/1; 174/137 B; 106/900
[58] Field of Search ..................... 524/862, 731; 528/15, 25, 31; 523/122; 424/401, 405, 70.12, 76.8, 76.1, 65, 63, 64; 174/1, 137 B; 106/900

[56] References Cited

U.S. PATENT DOCUMENTS

| | | | |
|---|---|---|---|
| 3,188,299 | 6/1965 | Chalk | 528/15 |
| 3,198,766 | 8/1965 | Nitzsche et al. | 528/15 |
| 3,867,343 | 2/1975 | Garden | 528/15 |
| 4,077,937 | 3/1978 | Sato et al. | 528/15 |
| 4,477,641 | 10/1984 | Matsumoto | 528/15 |
| 4,665,148 | 5/1987 | Wong | 528/15 |
| 4,752,398 | 6/1988 | Holbein et al. | 210/679 |
| 4,837,401 | 6/1989 | Hirose et al. | 525/364 |
| 4,925,895 | 5/1990 | Heeks et al. | 524/714 |
| 5,654,362 | 8/1997 | Schulz | 524/862 |

*Primary Examiner*—Margaret W. Glass Moore
*Attorney, Agent, or Firm*—James L. De Cesare

[57] ABSTRACT

A method of thickening solvents involves reacting (A) an ≡Si—H containing polysiloxane with (B) an alkene such as an alpha, omega-diene; conducting the reaction in the presence of a platinum catalyst and (C) a solvent; continuing the reaction until a gel is formed by crosslinking and addition of ≡Si—H across double bonds in the alpha, omega-diene; adding additional solvent and a post cure terminating agent to the gel; and subjecting the solvent, the post cure terminating agent, and the gel to shear force until a paste is formed. The post cure terminating agent is an amino acid ester, preferably a sulfur containing amino acid ester, such as methionine methyl ester, methionine ethyl ester, cysteine methyl ester, cysteine ethyl ester, and cystine dimethyl ester.

12 Claims, No Drawings

TERMINATING POST CURE WITH AMINO ACID ESTERS

CROSS-REFERENCE TO RELATED APPLICATIONS

This application is an improvement in methods generally described in a prior application U.S. Ser. No. 08/618,616, filed on Mar. 20, 1996, entitled "Silicone Oils and Solvents Thickened by Silicone Elastomers", now U.S. Pat. No. 5,654,362, which issued on Aug. 5, 1997. The prior application is assigned to the same assignee as this application. The prior application is considered incorporated herein by reference thereto, and will be referred to hereinafter as the '362 patent.

BACKGROUND OF THE INVENTION

This invention is directed to methods for the termination of post cure occurring in the thickening of siloxanes with silicone elastomers.

In the '362 patent, silicone elastomers are used in the thickening of silicone fluids and organic solvents. These elastomers are formed by a hydrosilylation reaction between a multifunctional ≡SiH siloxane and an α,ω-diene.

According to the '362 patent, one scheme representative of a process that can be used in making a silicone elastomer suitable in thickening a low viscosity fluid is shown below:
Step 1—Gelation
α,ω-diene+≡Si—H Siloxane+Fluid+Pt Catalyst→Gel
Step 2—Shear & Swell
Gel+More Fluid→Paste When a network is formed in such a reaction, we have determined that steric hindrance of the crosslinked structure prevents the reaction from reaching completion. This is believed to be due to the fact that a small amount of residual functionality will remain even after long reaction times, and that unreacted functionalities will tend to meet each other when the gel is sheared and swollen. We have termed the phenomenon post cure. Because residual reactivity causes smooth pasty products to gel once again, post cure should be eliminated in order to maintain a finer appearance and a more flowable rheology of the final paste product.

This can be achieved, according to our invention, by deactivating the platinum (Pt) catalyst with an amino acid ester post cure terminating agent, most preferably a sulfur containing amino acid ester.

BRIEF SUMMARY OF THE INVENTION

We have discovered that the post cure caused by the residual crosslinking hydrosilylation reactions which typically occur in the preparation of silicone elastomers can be terminated by introducing a strong platinum complexing ligand in order to deactivate the platinum catalyst. The strong platinum complexing ligand is preferably an amino acid ester, and most preferably is a sulfur containing amino acid ester. In our method, the resulting product has not been found to be contaminated by any toxic ingredients. This is an important feature, advantage, and benefit, when such products are intended for use in the personal care or health care arenas.

These and other features of our invention will become apparent from a consideration of the detailed description.

DETAILED DESCRIPTION OF THE INVENTION

As noted above, post cure caused by residual crosslinking hydrosilylation reactions occurring in silicone elastomers can be terminated by introducing a strong platinum complexing or deactivating amino acid based ligand.

In a copending, allowed U.S. patent application Ser. No. 08/964,546, filed in the name of one co-inventor herein Shizhong Zhang, on Nov. 5, 1997, entitled "Quenching Post Cure", and assigned to the same assignee as the present application, co-inventor Zhang discovered that certain strong platinum coordinating ligands were effective in terminating post cure by deactivating the functioning of the catalyst used in the preparation of silicone elastomers.

Suitable ligands suggested by Zhang include phosphines, amines, and organic sulfides. Representative ligands according to Zhang are trialkyl and triaryl phosphines such as triphenylphosphine $PPh_3$; amines, diamines, and triamines such as n-butylamine $CH_3(CH_2)_3NH_2$, triethanolamine $(HOCH_2CH_2)_3N$, and tetramethylethylenediamine $(CH_3)_2NCH_2CH_2N(CH_3)_2$; and organic sulfides such as ethyl phenyl sulfide $C_6H_5SC_2H_5$.

Zhang determined that by adding one equivalent or more of a ligand at the shear & swell step in the process, any crosslinking reactions can be terminated, and that therefore no post cure would occur.

However, we have determined that many strong ligands to platinum, such as those ligands suggested by Zhang, tend to be toxic, and so their presence, even in small amounts, may not be suitable in some applications, i.e., as in for example, personal care and health care products.

Accordingly, our improvement for the termination of post cure caused by residual crosslinking hydrosilylation reactions in silicone elastomers involves introducing a small amount, i.e., about one equivalent or more, of a strong platinum complexing ligand such as an amino acid ester. Especially preferred ligands according to our invention are sulfur containing amino acid esters such as methionine methyl ester $CH_3SCH_2CH_2CH(NH_2)COOCH_3$, methionine ethyl ester $CH_3SCH_2CH_2CH(NH_2)COOC_2H_5$, cysteine methyl ester $HSCH_2CH(NH_2)COOCH_3$, cysteine ethyl ester $HSCH_2CH(NH_2)COOC_2H_5$, and cystine dimethyl ester $\{-SCH_2CH(NH_2)COOCH_3\}_2$.

As a result, we have found that the platinum catalyst can be deactivated and that further crosslinking reaction will be difficult to occur in the resulting product. Our method is not only effective but it is also less hazardous since naturally occurring amino acid derivatives are employed. This is an important feature when the resulting product is intended for application in the personal care or health care arenas.

Because amine and sulfide functionality are good binding ligands for platinum, amino acid esters have in their free base form amino groups available to complex platinum catalysts in a hydrosilylation reaction. Even more importantly, however, where the amino acid esters contain sulfur, as in the case of methionine methyl ester, methionine ethyl ester, cysteine methyl ester, cysteine ethyl ester, and cystine dimethyl ester, the sulfide deactivates platinum catalysts even more effectively.

For purposes of our invention, it is preferred that the amino acids not be in zwitterionic form. Rather they should be derivatized to other forms, such as an ester, in order that they are rendered more compatible in silicone and organic systems. In addition, the amino acid derivatives should be in free base form, and not the ammonium salt form, so that they are more compatible in silicone and organic systems and have amino groups available to complex the platinum Pt catalyst. Alternatively, the amino acid derivatives can be converted to a free base form by a simple acid-base reaction after being mixed in the system.

The following examples are set forth in order to illustrate our invention in more detail.

EXAMPLE 1

A gel was prepared using the following ingredients:
(i) 50 g of an ≡SiH siloxane having an average structure represented by $Me_3SiO(Me_2SiO)_{93}(MeHSiO)_6SiMe_3$
(ii) 260 g of decamethylcyclopentasiloxane (hereafter D5)
(iii) 1.78 g of 1,5-hexadiene, and
(iv) 0.60 g of Karstedt's catalyst with a Pt content of 0.52%.

Karstedt's catalyst is a preferred platinum catalyst, and is described in Karstedt's U.S. Pat. Nos. 3,715,334 and 3,814,730, which are incorporated herein by reference. According to these patents, Karstedt's catalyst is a platinum divinyl tetramethyl disiloxane complex, typically containing about 0.5–1.0 weight percent of platinum, carried in a solvent such as toluene.

A mixture of the above ingredients was stirred in a capped container and heated at 60° C. until it gelled. The gel was heated in a 65–70° C. oven for one hour. The gel was sheared and swollen with additional D5, forming a silicone paste containing 10% of the elastomer. A methionine methyl ester solution (0.5 wt % of the active) 117 mg, was added and mixed with 117 g of the silicone paste. The methionine content was 5 ppm in the silicone paste. The resulting product had a viscosity of 176,000 cP (mpa•s) two hours after it had been prepared. One day later, it was noted that the paste had remained smooth, and that the viscosity had increased only slightly to 190,000 cP (mPa•s). The viscosity was measured using a Brookfield DV-II Viscometer having a TC-type spindle operated at a speed of 2.5 rpm (0.26 rad/s).

EXAMPLE 2A—COMPARATIVE EXAMPLE

Another gel was prepared according to Example 1, sheared, and swollen to form a silicone paste containing 10% of the elastomer in D5. No sulfur containing amino acid ester was added. The silicone paste was placed in a jar and the silicone paste gelled to a semisolid after about 12 hours.

EXAMPLE 2B—COMPARATIVE EXAMPLE

A third gel was prepared according to Example 1, sheared, and swollen to form a silicone paste containing 10% of the elastomer in D5. Instead of adding a sulfur containing amino acid ester as in Comparatve Example 2-A, a triphenylphosphine solution (0.5 wt % of the active) 95 mg, was mixed with 117 g of the silicone paste. The triphenylphosphine content in the silicone paste was 4.1 ppm. The viscosity of the silicone paste two hours after it had been prepared was 290,000 cP (mPa•s). One day later, it was observed that the silicone paste had become a soft gel, and that it had a viscosity of 330,000 cP (mPa•s). The viscosity in this example was measured in the same way as in Example 1. This comparative example indicates that a similar weight of methionine methyl ester stops post cure more effectively than triphenylphosphine.

Our invention is useful in any method involving silicone elastomers prepared by a crosslinking reaction between (A) ≡Si—H containing polysiloxanes and (B) an alkene such as an alpha, omega-diene, in the presence of a platinum catalyst and (C) a low molecular weight linear or cyclic polysiloxane. Such elastomers can be swollen with the low molecular weight polysiloxane under a shear force.

Typically, the ≡Si—H containing polysiloxane (A) is a polymer represented by the formula $R_3SiO(R'_2SiO)_a(R''HSiO)_bSiR_3$ designated herein as type $A^1$ and polymers of the formula $HR_2SiO(R'_2SiO)_cSiR_2H$ or formula $HR_2SiO(R'_2SiO)_a(R''HSiO)_bSiR_2H$ designated herein as type $A^2$. In these formulas, R, R', and R", are alkyl groups with 1–6 carbon atoms; a is 0–250; b is 1–250; and c is 0–250. The molar ratio of compounds $A^2:A^1$ is 0–20, preferably 0–5. In most preferred embodiments, compounds of types $A^1$ and $A^2$ are used in the reaction, however, it is possible to conduct the reaction using only compounds of type $A^1$.

The term alkene is intended herein to include and most preferably comprises an alpha, omega-diene (B) of the formula $CH_2=CH(CH_2)_xCH=CH_2$ where x is 1–20. Representative alpha, omega-dienes are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

The term alkene is also intended to include siloxane monomers or polymers containing two or more terminal alkenyl groups; two or more pendant alkenyl groups; or two or more terminal and pendant groups. One suitable siloxane is tetramethyldivinyldisiloxane, for example.

These addition and crosslinking reactions require a catalyst to effect reaction between the ≡SiH containing polysiloxane and the alpha, omega-diene. Suitable catalysts are Group VIII transition metals, i.e., the noble metals. Such noble metal catalysts are described in U.S. Pat. No. 3,923,705, incorporated herein by reference to show platinum catalysts. A preferred platinum catalyst is Karstedt's catalyst described above.

Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are typically used in amounts from 0.00001–0.5 parts per 100 weight parts of the ≡SiH containing polysiloxane, preferably 0.00001–0.02 parts, most preferably 0.00001–0.002 parts.

The phrase low molecular weight silicone oil (C) is intended to include (i) low molecular weight linear and cyclic volatile methyl siloxanes, (ii) low molecular weight linear and cyclic volatile and non-volatile alkyl and aryl siloxanes, and (iii) low molecular weight linear and cyclic functional siloxanes. Most preferred, however, are low molecular weight linear and cyclic volatile methyl siloxanes (VMS).

VMS compounds correspond to the average unit formula $(CH_3)_aSiO_{(4-a)/2}$ in which a has an average value of two to three. The compounds contain siloxane units joined by ≡Si—O—Si≡ bonds. Representative units are monofunctional "M" units $(CH_3)_3SiO_{1/2}$ and difunctional "D" units $(CH_3)_2SiO_{2/2}$.

The presence of trifunctional "T" units $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have the formula $(CH_3)_3SiO\{(CH_3)_2SiO\}_ySi(CH_3)_3$. The value of y is 0–5. Cyclic VMS have the formula $\{(CH_3)_2SiO\}_z$. The value of z is 3–6. Preferably, these volatile methyl siloxane have a boiling point less than about 250° C. and a viscosity of about 0.65–5.0 centistoke (mm²/s).

Representative linear volatile methyl siloxanes are hexamethyldisiloxane (MM) with a boiling point of 100° C., viscosity of 0.65 mm²/s, and formula $Me_3SiOSiMe_3$; octamethyltrisiloxane (MDM) with a boiling point of 152° C., viscosity of 1.04 mm²/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm$^2$/s, and formula Me$_3$SiO (Me$_2$SiO) $_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$.

Representative cyclic volatile methyl siloxanes are hexamethylcyclotrisiloxane (D$_3$) a solid with a boiling point of 134° C. and formula $\{(Me_2)SiO\}_3$; octamethylcyclotetrasiloxane (D$_4$) with a boiling point of 176° C., viscosity of 2.3 mm$^2$/s, and formula $\{(Me_2)SiO\}_4$; decamethylcyclopentasiloxane (D$_5$) with a boiling point of 210° C., viscosity of 3.87 mm$^2$/s, and formula $\{(Me_2)SiO\}_5$; and dodecamethylcyclohexasiloxane (D$_6$) with a boiling point of 245° C., viscosity of 6.62 mm$^2$/s, and formula $\{(Me_2)SiO\}_6$.

Representative branched volatile methyl siloxanes and are heptamethyl-3-{(trimethylsilyl)oxy}trisiloxane (M$_3$T) with a boiling point of 192° C., viscosity of 1.57 mm$^2$/s, and formula C$_{10}$H$_{30}$O$_3$Si$_4$; hexamethyl-3,3,bis {(trimethylsilyl)oxy} trisiloxane (M$_4$Q) with a boiling point of 222° C., viscosity of 2.86 mm$^2$/s, and formula C$_{12}$H$_{36}$O$_4$Si$_5$; and pentamethyl {(trimethylsilyl)oxy} cyclotrisiloxane (MD$_3$) with the formula C$_8$H$_{24}$O$_4$Si$_4$.

Our process can include the use of low molecular weight linear and cyclic volatile and non-volatile alkyl and aryl siloxanes. Representative linear polysiloxanes are compounds of the formula R$_3$SiO(R$_2$SiO)$_y$SiR$_3$, and representative cyclic polysiloxanes are compounds of the formula (R$_2$SiO)$_z$. R is an alkyl group of 1–6 carbon atoms, or an aryl group such as phenyl. The value of y is 0–80, preferably 0–20. The value of z is 0–9, preferably 4–6. These polysiloxanes have a viscosity generally in the range of about 1–100 centistoke (mm$^2$/s).

Other representative low molecular weight non-volatile polysiloxanes have the general structure:

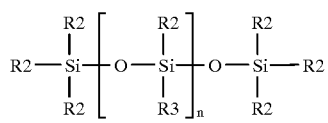

where n has a value to provide polymers with a viscosity in the range of about 100–1,000 centistoke (mm$^2$/sec).

R$^2$ and R$^3$ are alkyl radicals of 1–20 carbon atoms, or an aryl group such as phenyl. Typically, the value of n is about 80–375. Illustrative polysiloxanes are polydimethylsiloxane, polydiethylsiloxane, polymethylethylsiloxane, polymethylphenylsiloxane, and polydiphenylsiloxane.

Low molecular weight functional polysiloxanes can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

Our invention is not limited to swelling silicone elastomers with only low molecular weight polysiloxanes. Other types of solvents can swell the silicone elastomer. Thus, a single solvent or a mixture of solvents may be used.

By solvent we mean (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Makers and Painters (VM&P) naphtha, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

We further intend to encompass by the term solvent, volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, we intend the term solvent to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Carrying out of the basic process over which our invention is an improvement, i.e., the basic process being the one generally represented by the '362 patent, is a matter of combining the ≡SiH containing polysiloxane(s), the alpha, omega-diene, the low molecular weight silicone oil or other solvent, and the catalyst; and mixing these ingredients at room temperature until a gel is formed.

Additional amounts of the low molecular weight silicone oil or solvent are then added to the gel, and the resulting mixture is subjected to shear force to form the paste. Any type of mixing and shearing equipment may be used to perform these steps such as a batch mixer, planetary mixer, single or multiple screw extruder, dynamic or static mixer, colloid mill, homogenizer, sonolator, or a combination thereof.

Typically, that basic process uses approximately a 1:1 molar ratio of ≡Si—H containing polysiloxane and alpha, omega-diene. Useful materials may also be prepared by carrying out the basic process with an excess of either the ≡Si—H containing polysiloxane or the alpha, omega-diene, but this is a less efficient use of the materials. The remainder of the composition comprises the low molecular weight silicone oil or other solvent in amounts generally within the range of about 65–98 percent by weight of the composition, preferably about 80–98 percent by weight.

As noted above, our improvement resides in the feature of adding to the basic process one equivalent or more of a post cure terminating agent to deactivate the platinum catalyst, at or during the shear & swell step in the basic process.

The silicone elastomer, silicone gel, and silicone paste compositions of our invention have particular value in the personal care arena. Because of the unique volatility characteristics of the VMS component of these compositions, they can be used alone, or blended with other cosmetic fluids, to form a variety of over-the-counter (OTC) personal care products.

Thus, they are useful as carriers in antiperspirants and deodorants, since they leave a dry feel, and do not cool the skin upon evaporation. They are lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss and drying time, and provide conditioning benefits.

In cosmetics, they will function as leveling and spreading agents for pigments in make-ups, color cosmetics, foundations, blushes, lipsticks, lip balms, eyeliners, mascaras, oil removers, color cosmetic removers, and powders. They are useful as delivery systems for oil and water soluble substances such as vitamins. When incorporated into sticks, gels, lotions, aerosols, and roll-ons, the compositions impart a dry, silky-smooth, payout.

In addition, the compositions exhibit a variety of advantageous and beneficial properties such as clarity, shelf stability, and ease of preparation. Hence, they have wide application, but especially in antiperspirants, deodorants, in perfumes as a carrier, and for conditioning hair.

Our silicone elastomers, gels, and pastes have uses beyond the personal care arena, including their use as a filler or insulation material for electrical cable, a soil or water barrier for in-ground stabilization, or as a replacement for epoxy materials used in coil-on-plug designs in the electronics industry.

They are also useful as carrier for crosslinked silicone rubber particles. In that application, (i) they allow ease of incorporation of the particles into such silicone or organic phases as sealants, paints, coatings, greases, adhesives, antifoams, and potting compounds; and (ii) they provide for modifying rheological, physical, or energy absorbing properties of such phases in either their neat or finished condition.

In addition, our silicone elastomers, gels, and pastes are capable of functioning as carriers for pharmaceuticals, biocides, herbicides, pesticides, and other biologically active substances; and can be used to incorporate water and water-soluble substances into hydrophobic systems. Examples of some water-soluble substances are salicylic acid, glycerol, enzymes, and glycolic acid.

Other variations may be made in monomers, polymers, copolymers, compounds, compositions, and methods described herein without departing from the essential features of our invention. The forms of our invention are exemplary only and not intended as limitations on their scope as defined in the appended claims.

We claim:

1. A method of thickening solvents comprising reacting (A) an ≡Si—H containing polysiloxane of formula $R_3SiO(R'_2SiO)_a(R''HSiO)_bSiR_3$ and optionally an ≡Si—H containing polysiloxane of formula $HR_2SiO(R'_2SiO)_cSiR_2H$ or formula $HR_2SiO(R'_2SiO)_a(R''HSiO)_bSiR_2H$ where R, R', and R'' are alkyl groups of 1–6 carbon atoms; a is 0–250; b is 1–250; and c is 0–250; with (B) an alkene; conducting the reaction in the presence of a platinum catalyst and (C) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; continuing the reaction until a gel is formed; adding additional solvent and a post cure sulfur containing amino acid ester terminating agent selected from the group consisting of methionine methyl ester, methionine ethyl ester, cysteine methyl ester, cysteine ethyl ester and cystine dimethyl ester to the gel; and subjecting the solvent, the post cure terminating agent, and the gel to shear force until a paste is formed.

2. A paste prepared according to the method in claim 1.

3. A product containing the paste of claim 2 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, and cosmetic removers.

4. A product containing the paste of claim 2 and a material selected from the group consisting of crosslinked silicone rubber particles, pharmaceuticals, biocides, herbicides, pesticides, water, and water-soluble substances.

5. A method of treating hair or skin comprising applying to the hair or skin a product of claim 3.

6. A method of modifying rheological, physical, or energy absorbing properties, of silicone or organic phases selected from the group consisting of sealants, paints, coatings, greases, adhesives, antifoams, and potting compounds, comprising incorporating therein the paste of claim 2 containing crosslinked silicone rubber particles.

7. A method of filling or insulating an electrical cable comprising incorporating therein the paste of claim 2.

8. A method of stabilizing in-ground soil or water barriers comprising incorporating into soil the paste of claim 2.

9. A method of thickening solvents comprising reacting (A) an ≡Si—H containing polysiloxane of formula $R_3SiO(R'_2SiO)_a(R''HSiO)_bSiR_3$ and optionally an ≡Si—H containing polysiloxane of formula $HR_2SiO(R'_2SiO)_cSiR_2H$ or formula $HR_2SiO(R'_2SiO)_a(R''HSiO)_bSiR_2H$ where R, R', and R" are alkyl groups of 1–6 carbon atoms; a is 0–250; b is 1–250; and c is 0–250; with (B) an alpha, omega-diene of formula $CH_2=CH(CH_2)_xCH=CH_2$ where x is 1–20; conducting the reaction in the presence of a platinum catalyst and (C) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; continuing the reaction until a gel is formed by crosslinking and addition of ≡Si—H across double bonds in the alpha, omega-diene; adding additional solvent and a post cure terminating agent to the gel; the post cure terminating agent being a sulfur containing amino acid ester selected from the group consisting of methionine methyl ester, methionine ethyl ester, cysteine methyl ester, cysteine ethyl ester, and cystine dimethyl ester; and subjecting the solvent, the post cure terminating agent, and the gel to shear force until a paste is formed.

10. A paste prepared according to the method in claim 9.

11. A product containing the paste of claim 10 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, and cosmetic removers.

12. A method of treating hair or skin comprising applying to the hair or skin a product of claim 11.

* * * * *